United States Patent [19]

El Khadem et al.

[11] 4,302,449
[45] Nov. 24, 1981

[54] CARMINOMYCIN ANALOGUE

[75] Inventors: Hassan S. El Khadem, Houghton; David L. Swartz, Midland, both of Mich.

[73] Assignee: Board of Control of Michigan Technological University, Houghton, Mich.

[21] Appl. No.: 183,197

[22] Filed: Sep. 2, 1980

[51] Int. Cl.$^3$ ............... A61K 31/70; C07H 15/24
[52] U.S. Cl. ............................ 424/180; 536/17 A
[58] Field of Search ................ 536/17 R, 17 A; 424/180

[56] References Cited

U.S. PATENT DOCUMENTS 4,188,377  2/1980  Suarato et al. ............... 536/17 A
4,189,568  2/1980  Johnson et al. ............... 536/17 A
4,201,773  5/1980  Horton et al. ............... 536/17 A

OTHER PUBLICATIONS

Khadem et al., Carbohydrate Res., vol. 65, C1–C2 (1978).
Khadem et al., J. Med. Chem., vol. 20, 957–960 (1977).
Fuchs et al., Carbohydrate Res., vol. 57, C36–C39 (1977).
Khadem et al., Carbohydrate Res., vol. 58, 230–234 (1977).

*Primary Examiner*—Johnnie R. Brown
*Assistant Examiner*—Blondel Hazel

[57] ABSTRACT

A novel anthracycline glycoside 2-deoxy-L-fucopyranosyl carminomycinone which is effective for inhibiting the growth of tumors such as leukemia L1210.

2 Claims, No Drawings

CARMINOMYCIN ANALOGUE

BACKGROUND OF THE INVENTION

1. Field of the Invention

This invention relates to a new anthracycline glycoside antineoplastic agent and, more particularly, to a new oxygen analogue of the anthracycline antibiotic carminomycin.

2. Prior Art

As described in M. G. Brazhnikova et al., *J. Antibiot.*, 27:254–259 (1974), G. F. Gause et al, *Cancer Chemother. Rep.* 58:255–256 (1974), M. C. Wani et al, *J. Am. Chem. Soc.* 97:5955–5956 (1975) and West German Pat. No. 2,362,707, the anthracycline glycoside carminomycin is known to be a clinically useful antineoplastic agent. However, it produces certain undesirable side effects, common to many antineoplastics agents, which limit its use in chemotherapy. In particular, it produces a cumulative, dose-related cardiotoxicity which limits the total dosage that can be administered to a patient and the duration of treatment.

Preparation of a glycoside of daunorubicin is described in E. F. Fuchs et al, *Carbohydr. Res.*, 57: C36 (1977). Preparation of glycosides of ε-rhodomycinone is described in H. S. El Khadem et al, *J. Med. Chem.*, 20:957–960 (1977). Preparation of 2-deoxy-L-fucopyranosyl-ε-pyrromycinone and 2-deoxy-D-erythro-pentopyransoly-ε-pyrromycinone, - cdaunomycinone, and - carminomycinone and their dio-O-acetyl derivatives is described in H. S. El Khadem, *Carbohydr. Res.*, 65: C1 (1978).

SUMMARY OF THE INVENTION

The present invention provides a new oxygen analogue of carminomycin which can be represented by the following formula:

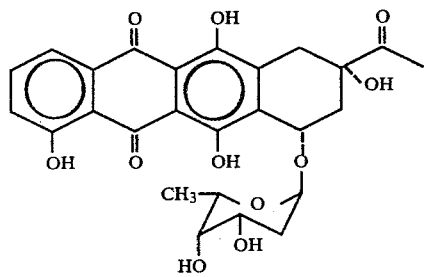

This carminomycin analogue can be prepared by coupling an appropriate glycosyl halide, namely, 3,4-di-O-acetyl-2,6-dideoxy-α-L-lyxo-hexopyranosyl bromide, or the corresponding chloride, to carminomycinone. The resulting acetylated blocked glycoside intermediate is deacetylated to produce the above oxygen analogue of carminomycin which is effective for inhibiting the growth of tumors such as leukemia L1210.

The invention also provides a method for inhibiting the growth of certain mammalian tumors such as L1210 leukemia by administering therapuetically effective amounts of the above compound to experimental animals afflicted with such tumors.

DETAILED DESCRIPTION

The overall reaction scheme of a preferred process for preparing the novel carminomycin analogue of the invention can be represented as follows:

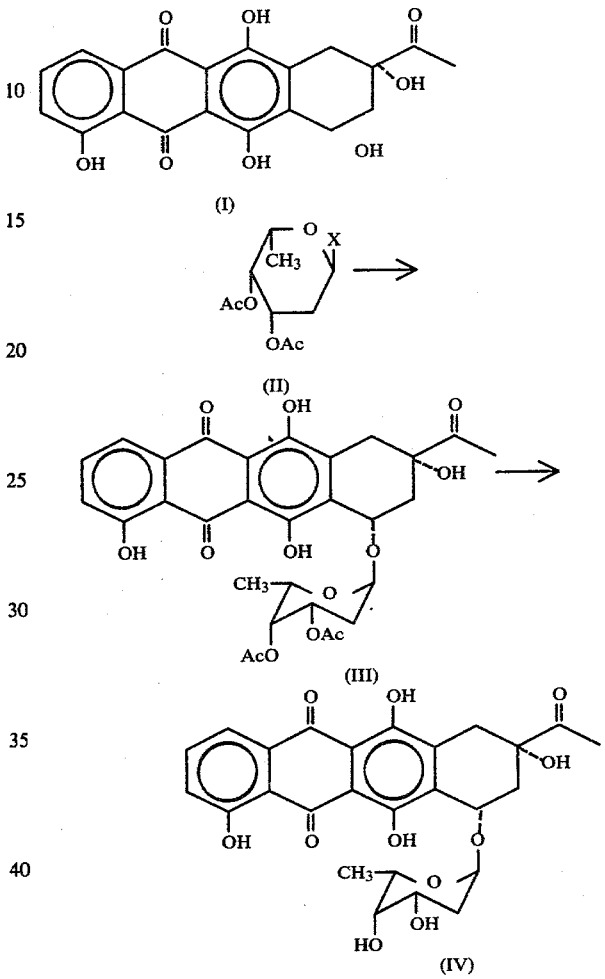

wherein X is Br or Cl.

The starting compound carminomycinone (I) can be prepared in a conventional manner such as by hydrolyzing carminomycine. This can be accomplished by refluxing a 0.1 N hydrochloric solution of carminomycin for 2–3 hours and filtering the precipitate carminomycinone crystals from the solution.

The glycosyl halide 3,4-di-O-acetyl-2,6-dideoxy-α-L-lyxo-hexopyranosyl bromide or chloride (II) coupled with carminomycinone can be prepared in the manner as described in H. S. El Khadem et al, *Carbohydr. Res.*, 58:230–234 (1977). That is, L-fucose tetraacetate is treated with hydrogen bromide in acetic acid to obtain the corresponding glycosyl bromide which is treated with an activated zinc dust suspension at a reduced temperature, the cold mixture filtered and the filtrate extracted with chloroform or the like. The resulting di-O-acetyl-L-fucal is treated with a dry stream of hydrogen bromide or hydrogen chloride to produce the desired glycosyl halide.

The coupling reaction is carried out by refluxing one molar equivalents of carminomycinone and the glycosyl halide under Koenig-Knorr conditions using a mercuric bromide-mercuric cyanide catalyst. The reaction product is filtered to remove solids and the mercuric salts. The filtrate is evaporated to dryness to remove the solvent. The solid residue is dissolved in a suitable solvent, such as chloroform, and the resulting solution is washed to remove remaining mercuric salts. After the solution is evaporated to dryness, the resulting solid residue is dissolved in a suitable solvent, such a diethyl ether, and sugar components which do not react with carminomycinone are removed in a suitable manner, such as with a column chromatograph, to yield the blocked acetylated glycoside intermediate (III).

The glycoside intermediate (III) is deacetylated in a suitable manner to produce the carminomycin analogue of the invention. This can be accomplished by dissolving the acetylated glycoside in a suitable solvent, such as methanol, and adding the solution to a sodium methoxide-methanol solution containing an excess of sodium methoxide. The desired carminomycinone analogue 2-deoxy-L-fucopyranosyl carminomycinone (IV) is extracted by chloroform or the like.

The compound of the invention can be used as an active ingredient in pharmaceutical compositions including a pharmaceutically acceptable carrier. Such compositions could also include one or more active antibacterial and/or antineoplastic agents and may be in any form suitable for the desired mode of administration. For instance, the pharmaceutical composition can be in a solid form for oral administration, such as tablets, powders, granules or capsules, liquid form for oral administration such as syrups, solutions or suspensions and liquid preparations for parenteral administration, such as solutions, emulsions, or suspensions.

The pharmaceutical composition is administered in dosages which provide a concentration of the carminomycinone glycoside greater than the minimum inhibitory concentration for the leukemia tumor. The actual dosage will vary depending on such things as the formulation of the composition, mode of administration, age, weight, diet and reaction sensitivities of the afflicted host, and severity of the tumor. It is well within the skill of the art, after reviewing the guidelines disclosed herein, to determine the optimum dosage for a given situation by using conventional dosage tests.

Without further elaboration, it is believed one skilled in the art can, by using the preceeding description, utilize the present invention in its fullest extent. The following examples are presented for the purpose of illustration and should not be construed as limitations to the invention.

EXAMPLE 1

Preparation of 2-deoxy-L-fucopyranosyl carminomycinone 300 mg of carminomycin in 30 ml of 0.1 N hydrochloric acid was refluxed with stirring for 3 hours. This solution was cooled and filtered. The wet red crystals were dried in a vacuum desiccator over sodium hydroxide overnight to yield about 200 mg of carminomycinone (I).

A mixture comprising 200 mg carminomycinone, 1.0 g finely divided molecular sieves 3A, 200 mg mercuric bromide, 20 mg mercuric cynnanide, 200 mg 3,4-di-O-acetyl-2,6-dideoxy-α-lyxo hexopyranosyl bromide (II) and 20 ml tetrahydrofuran was refluxed with stirring for 1 hour. An additional 200 mg of the glycosyl bromide was added to the mixture and the mixture refluxed for another hour. The solution was filtered to remove the molecular sieves and the mercuric compounds and the sieves were washed with chloroform. The combined filtrates were evaporated to dryness, the solid residue dissolved in chloroform and the resulting solution was washed several times with a 20% potassium iodide solution to remove remaining mercuric compounds. The solution was then dried over anhydrous sodium sulfate and evaporated to dryness. The solid residue was dissolved in absolute diethyl ether containing a small amount of chloroform and the solution was applied to a silica gel column chromatograph (washed with absolute diethyl ether) to remove sugar components which had not reacted with carminomycinone. The blocked acetylated glycoside intermediate (III) was eluded with chloroform containing 3% methanol.

The glycoside-containing fractions from the chromatograph were evaporated to dryness. The solid residue was dissolved in 20 ml of methanol and the resulting solution was added to a freshly prepared, room temperature sodium methoxide/methanol solution containing an excess of sodium methoxide to deacetylate the glycoside. After 20 minutes, the solution was poured into a separatory funnel containing a sodium hydrogen sulfate solution and the desired oxygen analogue of carminomycin (IV) was extracted with chloroform. The extract was dried over anhydrous sodium sulfate and evaporated to dryness. The solid residue was dissolved in 40 ml of hot 95% methanol and the resulting solution was filtered and reduced in volume to about 10 ml. After cooling, the crystals were filtered and washed with ethanol and ether to yield about 100 mg of 2-deoxy-L-fucopyranosyl carminomycinone (IV) having a melting point of 228°–232° C. Elemental analysis of the material gave the following results:

Calculated weight percent for $C_{26}H_{26}O_{11}$, 0.5 $H_2O$: C=59.65, H=5.20. Found: C=59, H=4.91.

The structure for the glycoside (IV) was confirmed by its n.m.r. spectrum.

EXAMPLE 2

Bilogical Activity

The carminomycinone glycoside prepared by the procedure described in Example 1 was tested against transplanted mouse leukemia L 1210 according to the procedures described in *Cancer Chemother, Rep.*, 3:1–87, Part 3 (1972). Two experiments were conducted. The mice were given a single treatment in the first experiment and the mice were given both a single treatment and a daily injection for 9 days (QD 1→9) in the second experiment.

The test results are summarized in Table I. From these data, it can be seen that the survival time of tumor bearing animals was increased 86% over the control in the first experiment and at least one dose for each type of treatment in the second experiment increased the survival time by 71%.

From the foregoing description, one skilled in the art can easily ascertain the essential characteristics of the invention, and without departing from the spirit and scope thereof, can make various changes and modifications to adapt it to various usages.

We claim:

TABLE I

EFFECT OF CARMINOMYCINONE GLYCOSIDE (CG) ON L 1210 LEUKEMIA

| Experiment No. | Material | Treatment Regimen | Dose, mg/kg/day | MST, Days | Effect MST, % T/C | Average Weight Change, g | Survivors, Day 5 |
|---|---|---|---|---|---|---|---|
| 1 | CG | Once, Day 1 | 12.8 | 13.0 | 186 | −0.4 | 6/6 |
| | | ↓ | 6.4 | 9.5 | 136 | −1.1 | 6/6 |
| | | ↓ | 3.2 | 8.0 | 114 | −0.9 | 6/6 |
| | | ↓ | 1.6 | 7.5 | 107 | −0.8 | 6/6 |
| | | ↓ | 0.8 | 8.0 | 114 | +1.2 | 6/6 |
| | | ↓ | 0.4 | 7.0 | 107 | −0.8 | 6/6 |
| | Control (saline) | ↓ | — | 7.0 | — | +2.2 | 10/10 |
| 2 | CG | Once, Day 1 | 51.2 | 12.0 | 171 | −1.9 | 5/6 |
| | | ↓ | 25.6 | 11.5 | 164 | −1.2 | 6/6 |
| | | ↓ | 12.8 | 9.5 | 136 | +0.3 | 6/6 |
| | | ↓ | 6.4 | 11.0 | 157 | +0.7 | 6/6 |
| | | ↓ | 3.2 | 8.0 | 114 | +0.2 | 6/6 |
| | | ↓ | 1.6 | 9.0 | 129 | −0.6 | 6/6 |
| | | QD 1 → 9 | 12.8 | 8.0 | 114 | −1.6 | 5/6 |
| | | ↓ | 6.4 | 12.0 | 171 | −1.7 | 6/6 |
| | | ↓ | 3.2 | 11.0 | 157 | −0.3 | 5/6 |
| | | ↓ | 1.6 | 8.5 | 121 | −0.6 | 6/6 |
| | | ↓ | 0.8 | 8.0 | 114 | +2.3 | 6/6 |
| | | ↓ | 0.4 | 8.0 | 114 | +0.6 | 6/6 |
| | Control (saline) | | — | 7.0 | — | +1.9 | 10/10 |

Tumor Inoculum: $10^6$ ascites cells implanted i.p. into $BDF_1$ female mice.
Evaluation: MST = median survival time in days; % T/C = MST treated/MST control × 100.
Criteria: % T/C = 125 considered significant antitumor effect.

1. A compound having the formula:

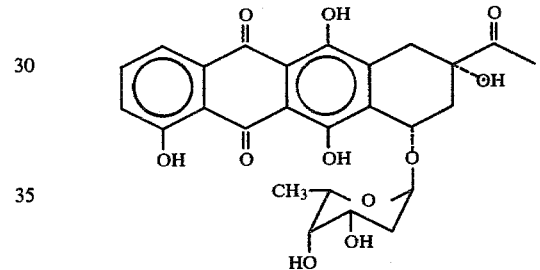

2. A method of inhibiting the growth of L 1210 leukemia tumors comprising administering to an experimental animal host afflicted with said tumor a composition including an amount of a compound according to claim 1 sufficient to inhibit the growth of said tumor and a pharmaceutically acceptable carrier.

* * * * *